United States Patent [19]

Jiang et al.

[11] Patent Number: 5,141,957
[45] Date of Patent: Aug. 25, 1992

[54] 1,4-BIS-(AMINO-HYDROXYALKYLAMINO)-ANTHRAQUINONES FOR INHIBITING PROTEIN KINASE C

[75] Inventors: Jack B. Jiang, Chapel Hill; Mary G. Johnson, Carrboro, both of N.C.

[73] Assignee: Sphinx Pharmaceuticals Corporation, Durham, N.C.

[21] Appl. No.: 609,416

[22] Filed: Nov. 5, 1990

Related U.S. Application Data

[63] Continuation-in-part of Ser. No. 608,248, Nov. 2, 1990, abandoned.

[51] Int. Cl.⁵ .................... C07C 97/24; A01N 37/00
[52] U.S. Cl. .................... 514/510; 514/561; 514/619; 514/647; 514/680; 552/238; 552/240; 552/243; 552/246; 552/251
[58] Field of Search ............. 552/238, 240, 243, 249, 552/251; 514/647, 510, 561, 619, 680

[56] References Cited

U.S. PATENT DOCUMENTS

| | | | |
|---|---|---|---|
| 1,540,733 | 6/1925 | Baddiley et al. | 552/260 |
| 2,411,148 | 11/1946 | Dickey et al. | 552/260 |
| 3,960,751 | 6/1976 | Moriyama et al. | 252/299 |
| 4,197,249 | 4/1980 | Murdock et al. | 552/243 |
| 4,310,666 | 1/1982 | Zee-Cheng et al. | 544/380 |
| 4,526,989 | 7/1985 | Murdock et al. | 549/316 |
| 4,540,788 | 9/1985 | Murdock | 546/264 |
| 4,598,155 | 7/1986 | Adam | 548/253 |
| 4,762,648 | 8/1988 | Stache et al. | 552/261 |
| 4,816,450 | 3/1989 | Bell et al. | 514/25 |
| 4,894,451 | 1/1990 | Krapcho et al. | 544/156 |

FOREIGN PATENT DOCUMENTS

| | | | |
|---|---|---|---|
| 3827974 | 2/1990 | Fed. Rep. of Germany | |
| 63-15853 | 1/1988 | Japan | 552/260 |
| 19818 | 5/1990 | Japan | |

OTHER PUBLICATIONS

Castagna et al. (1982), J. Biol. Chem. 257:7847.
Grunicke et al. (1989), Adv. Enzyme Regul. 28:201.
Tritton, et al. (199), Cancer Cells 2:95–102.
Schachtele et al. (1988), Biochem. Biophys. Res. Commun. 151:542.
Hannun et al. (1987), J. Biol. Chem. 262:13620.
Yamada et al. (1988), Biochem. Pharmacol. 37:1161.
McIntyre, et al. (1987), J. Biol. Chem. 262:15730.
Lambreth et al. (1988), J. Biol. Chem. 263:3818.
Pittet et al. (1987), J. Biol. Chem. 262:10072.
Gaudry et al. (1988), Immunology 63:715.
Wilson et al. (1986), J. Biol. Chem. 261:12616.
Fujita et al. (1986), Biochem. Pharmacol. 35:4555.
Berkow et al. (1987), J. Leukoc. Biol. 41:441.
Salzer et al. (1987), Biochem. Biophys. Res. Commun. 148:747.
Kramer et al. (1989), J. Biol. Chem. 262:5876.
Dewald et al. (1989), Biochem. J. 264:879.

*Primary Examiner*—C. Warren Ivy
*Assistant Examiner*—Raymond Covington
*Attorney, Agent, or Firm*—Woodcock, Washburn, Kurtz, Mackiewicz & Norris

[57] ABSTRACT

The present invention provides novel substituted anthraquinones having the formula

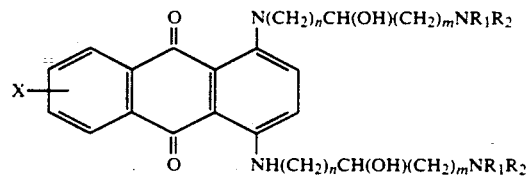

wherein
$R_1$ and $R_2$ are independently H, alkyl, aryl, or arylalkyl;
m and n are independently 1, 2, or 3;
X is H, OH, $NR_3R_4$, Cl, Br, I, F, alkyl, aryl alkoxy, aroxy, $COOR_5$, or $CONR_6R_7$;
$R_3$, $R_4$, $R_5$, $R_6$, and $R_7$ are independently H, lower alkyl or aryl useful for inhibiting protein kinase C and treating conditions related to, or affected by inhibition of protein kinase C, particularly cancer tumors, inflammatory disease, reperfusion injury, and cardiac dysfunctions related to reperfusion injury.

39 Claims, 2 Drawing Sheets

1,4-BIS-(AMINO-HYDROXYALKYLAMINO)-ANTHRAQUINONES FOR INHIBITING PROTEIN KINASE C

REFERENCE TO RELATED APPLICATIONS

The present application is a continuation-in-part application of U.S. application Ser. No. 608,248, filed Nov. 2, 1990 now abandoned in the names of Jack B. Biang and Mary George Johnson entitled "1,4-Bis-(Amino-Hydroxylalkylamino)-Anthraquinones For Inhibiting Protein Kinase C", the disclosures of which are hereby incorporated by reference as if fully set forth herein.

FIELD OF THE INVENTION

The present invention relates to the field of treatments for inflammatory and cardiovascular diseases, and chemotherapeutic agents. More particularly, the present invention relates to novel 1,4-bis-(amino-hydroxylalkylamino)-anthraquinones for inhibiting the enzyme protein kinase C.

BACKGROUND OF THE INVENTION

Protein kinase C (PKC) is a family of calcium stimulatable and phospholipid-dependent serine/threonine-specific protein kinases which play an important role in cellular growth control, regulation, and differentiation. protein kinase C is also fundamental to the processes involved in tumorigenicity, since it is the major high-affinity receptor for several classes tumor promoters as well as for endogenous cellular diacylglycerols. These tumor promoters also stimulate protein kinase C catalysis. Castagna et al. (1982) J. Biol. Chem. 257: 7847) reported direct activation of protein kinase C by tumor promoting phorbol esters. The mechanisms of protein kinase C action have been described in U.S. Pat. No. 4,816,450 issued Mar. 28, 1989 to Bell et al., the disclosures of which are specifically incorporated as if fully set forth herein. Protein kinase C is activated by diacylglycerol (DAG), a neutral lipid, and when activated will transfer the γ-phosphate of MgATP to a serine or threonine residue on a substrate protein.

Since the activation of protein kinase C have been implicated in several human disease processes, including cancer tumors, inflammation, and reperfusion injury, inhibition of protein kinase C should be of great therapeutic value in treating these conditions.

Protein kinase C inhibitors have been reported to potentiate the antitumor activity of cis-platin both in vitro and in vivo (Grunicke et al. (1989) Adv. Enzyme Regul. 28: 201; and German Offenlegungsschrift DE 3827974). In addition, it has been suggested that protein kinase C would be a potential target for therapeutic design because of its central role in cell growth (Tritton, T. R. and Hickman, J. A. Cancer Cells 2: 95–102 (1990)).

Protein kinase C inhibitors have been demonstrated to block platelet aggregation and release of neutrophil activating agents such as platelet activating factor (PAF)(Schachtele et al. (1988) Biochem. Biophy. Res. Commun. 151: 542; Hannun et al. (1987) J. Biol. Chem. 262: 13620; Yamada et al. (1988) Biochem. Pharmacol. 37: 1161). protein kinase C inhibitors have also been shown to inhibit neutrophil activation, and chemotactic migration (McIntyre et al. (1987) J. Biol Chem. 262: 15730; Lambreth et al. (1988) J. Biol. Chem. 263: 3818; Pittet et al. (1987) J. Biol. Chem. 262: 10072; and Gaudry et al. (1988) Immunology 63: 715), as well as neutrophil degranulation and release of proteolytic enzymes and reactive oxygen intermediates (Wilson et al. (1986) J. Biol. Chem. 261: 12616; Fujita et al. (1986) Biochem. Pharmacol. 35: 4555; Berkow et al. (1987) J. Leukoc., Biol. 41: 441; Salzer et al. (1987) Biochem. Biophys. Res. Commun. 148: 747; Kramer et al. (1989) J. Biol. Chem. 262: 5876; and Dewald et al. (1989) Biochem. J. 264: 879). Thus inhibitors of protein kinase C have the capability of blocking all three of the most significant mechanisms of pathogenesis associated with myocardial reperfusion injury, and should thus have a decided therapeutic advantage. Additionally, the inhibitory effect of protein kinase C inhibitors on keratinocytes, and on the oxidative burst in neutrophils will lead to an anti-inflammatory effect.

Substituted anthraquinones have been reported for various uses, including cancer treatment. U.S. Pat. No. 3,960,751 issued Jun. 1, 1976 to Moriyama et al. discloses substituted anthraquinones useful as pleochroic dyes. U.S. Pat. No. 4,598,155 issued Jul. 1, 1986 to Adam discloses tetrazole substituted anthraquinones useful as dyes.

U.S. Pat. No. 4,762,648 issued Aug. 9, 1988 to Stache et al. discloses mono-functional and bis-functional anthraquinone-(oxy-2,3-oxidopropanes) useful as intermediates in the preparation of drugs possessing β-receptor blocker action and as crosslinking agents in the preparation of polymers. The compounds also exhibit cytostatic activity.

Several patents disclose the use of substituted anthraquinones for treatment of neoplasms. U.S. Pat. No. 4,894,451 issued Jan. 16, 1990 to Krapcho et al. discloses unsymmetrical 1,4-bis-(aminoalkylamino)-anthracene-9,10-diones useful in the treatment of neoplasms. U.S. Pat. No. 4,310,666 issued Jan. 12, 1982 to Zee-Cheng et al discloses 1,4-bis-(substituted aminoalkylamino)-anthraquinones useful in the treatment of neoplasms. U.S. Pat. No. 4,526,989 issued Jul. 2, 1985 to Murdock et al discloses symmetrical 1,4-bis(substituted-amino)-5,8-dihydroxyanthraquinones useful as chelating agents and for inhibiting the growth of tumors. U.S. Pat. No. 4,197,249 issued Apr. 8, 1980 to Murdock et al also discloses symmetrical 1,4-bis(substituted-amino)-5,8-dihydroxyanthraquinones useful as chelating agents and for inhibiting the growth of tumors. U.S. Pat. No. 4,540,788 issued Sep. 10, 1985 to Murdock discloses 1,4-bis[aminoalkyl)amino]-9,10-anthracenediones and leuco bases thereof which are useful as chelating agents and for inducing regression of leukemia and/or inhibition of tumor growth in mammals. Japanese patent 19819 issued May 7, 1990 discloses substituted anthraquinones having substituents at positions 5 and 6 of the anthraquinone ring structure which are useful as antitumor agents alone or in combination with other antitumor agents.

German Offenlegungsschrift DE 3827974 A1 discloses therapeutic preparations comprising a protein kinase C inhibitor in combination with a lipid, a lipid analogue, a cytostatic agent or phospholipase inhibitor useful for cancer therapy. However, none of the protein kinase c inhibitors disclosed in this publication are substituted anthraquinones.

Although substituted anthraquinones have been reported for cancer treatments, substituted anthraquinones such as Mitoxantrone, are known to be associated with side effects, mainly immunosuppressive activity, and drug resistance. Accordingly novel cancer treatments that avoid some or all of these drawbacks are needed.

Further, inflammation and reperfusion injury, particularly pertaining to cardiac injury, are common conditions for which there exists no definitive treatment despite extensive research, and appropriate treatments for these conditions are needed.

SUMMARY OF THE INVENTION

The present invention provides novel substituted anthraquinones having formula I

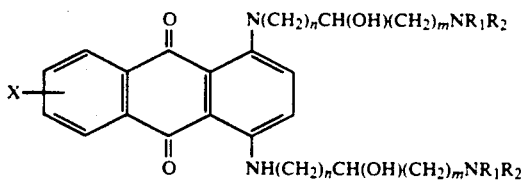

wherein $R_1$ and $R_2$ are independently, H, alkyl, aryl, or arylalkyl; m and n are independently 1, 2, or 3; X is H, OH, $NR_3R_4$, Cl, Br, I, F, alkyl, aryl alkoxy, aroxy, $COOR_5$, or $CONR_6R_7$; and $R_3$, $R_4$, $R_5$, $R_6$, and $R_7$ are independently H, lower alkyl or aryl.

The novel compounds of the invention are useful for inhibiting protein kinase C and are further useful for treating conditions related to, or affected by inhibition of protein kinase C, particularly cancer tumors, inflammatory disease, myocardial reperfusion injury, and cardiac dysfunctions related to reperfusion injury. Inhibition of protein kinase C can lead to inhibition of growth of tumor cells and can thereby produce an anti-tumor effect. Further, inhibition of protein kinase C can also lead to inhibition of the oxidative burst in neutrophils, platelet aggregation, and keratinocyte proliferation, whereby an anti-inflammatory effect is achieved. The inhibitory activities of the compounds of the invention against platelet aggregation, neutrophil activation, and neutrophil release demonstrate their usefulness in treating reperfusion injury, particularly myocardial reperfusion injury.

The compounds of the invention are expected to be particularly useful in the treatment of tumors resistant to treatment with other chemotherapeutic agents. Surprisingly, compounds of the invention are able to inhibit protein kinase C even in adriamycin or Mitoxantrone resistant cells, and thus are not cross-resistant with these chemotherapy agents.

The compounds of the invention appear to have no effect on cAMP dependent protein kinase C and should consequently have no effect on the metabolic pathways associated with stimulation of protein kinase C by cAMP.

The invention is more particularly pointed out in the appended claims and is described in its preferred embodiments in the following description.

DETAILED DESCRIPTION OF THE INVENTION

Figure 1:
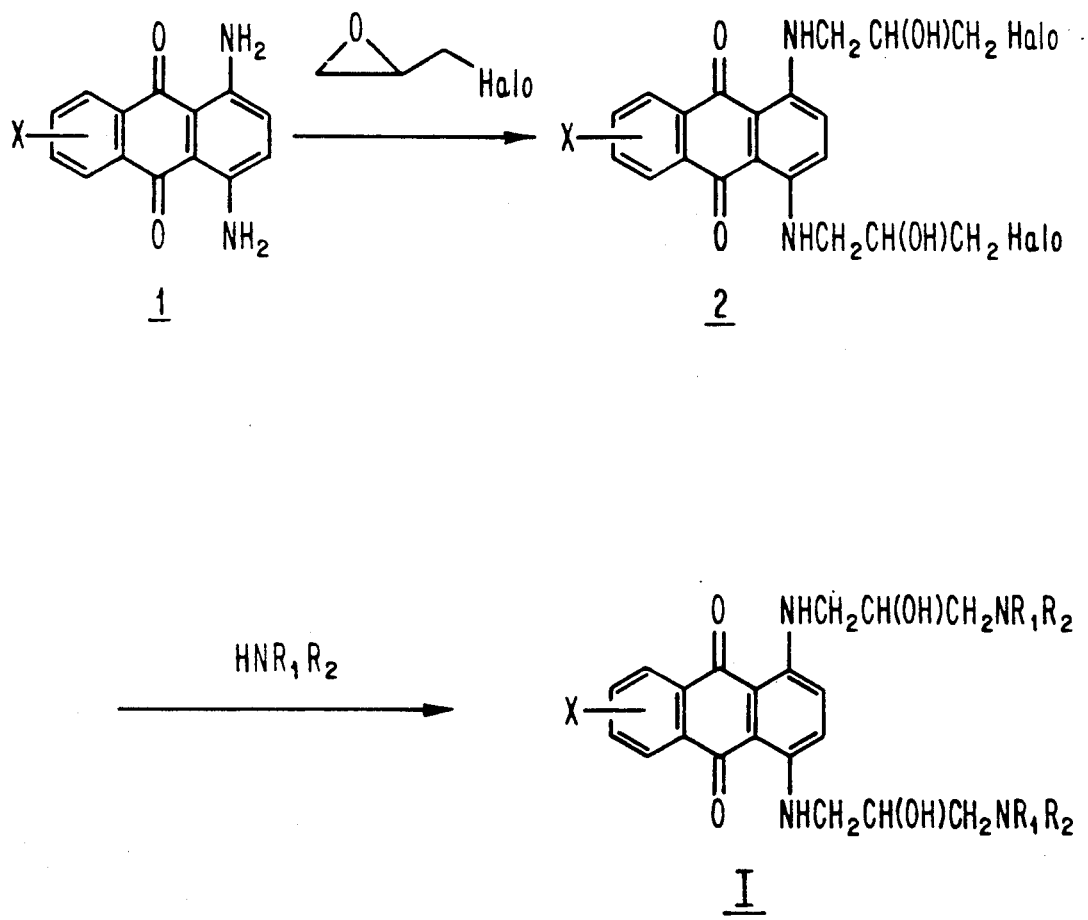
FIG. 1 shows the synthetic route of Scheme I which is used for synthesis of compounds of the invention.

The present invention provides novel substituted anthraquinones having formula I

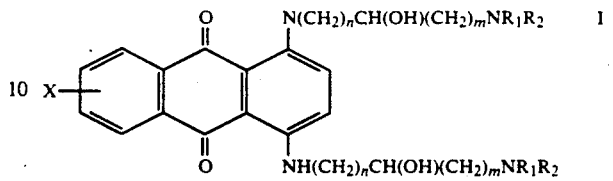

wherein $R_1$ and $R_2$ independently are preferably H, alkyl, aryl, or arylalkyl; more preferably H, lower alkyl (i.e. $C_1$-$C_6$ alkyl), or arylalkyl; most preferably H and arylalkyl. m and n independently are preferably an integer from 1-3; more preferably 1 or 2; most preferably 1. X is preferably H, OH, $NR_3R_4$, Cl, Br, I, F, $C_1$-$C_{10}$ alkyl, aryl alkoxy, aroxy, $COOR_5$, or $CONR_6R_7$, wherein $R_3$, $R_4$, $R_5$, $R_6$, and $R_7$ are independently H, lower alkyl (i.e. $C_1$-$C_6$ alkyl), or aryl. X is more preferably H, OH, Cl, Br, I, F, or alkoxy, more preferably X is H or OH.

As used herein, alkyl substituents include straight chain, branched and cyclic moieties, preferably straight chain species. While saturated species are preferred, unsaturated sites may find utility in some substituents. Alkaryl substituents are preferably substituted benzene moieties, with ortho, meta, and para substituents each believed to be useful. Multiple substitutions are similarly useful. Aralkyl substituents are preferably benzene substituted alkanes including benzyl, phenylethyl, phenylpropyl, etc.

The compounds of the invention are useful for treating conditions related to, or affected by inhibition of protein kinase C, particularly cancer tumors, inflammatory disease, reperfusion injury, and cardiac dysfunctions related to reperfusion injury. Accordingly, the invention provides methods and pharmaceutical compositions for inhibiting protein kinase C which comprise contacting protein kinase C with an inhibitory amount of a substituted anthraquinone compound of the invention. The pharmaceutical compositions of the invention comprise a substituted anthraquinone compound of the invention and a pharmaceutically acceptable carrier of diluent.

The invention also provides methods of inhibiting an oxidative burst in neutrophils which comprise contacting a neutrophil with a protein kinase C inhibitory concentration of a substituted anthraquinone compound of the invention, or contacting the neutrophil with an amount of a compound of the invention effective to inhibit such oxidative outburst.

The invention further provides methods for treating inflammation which comprise administering to a mammal suffering from inflammation a protein kinase C inhibitory concentration of a substituted anthraquinone compound of the invention, or administering to the mammal an amount of a compound of the invention effective to inhibit inflammation.

The invention additionally provides methods for inhibiting growth of mammalian tumor cells which comprises contacting a mammalian tumor cell with a protein kinase C inhibitory concentration of a substituted anthraquinone compound of the invention, or contacting the tumor cell with an amount of a compound of the invention effective to inhibit growth of the tumor cell.

An additional embodiment of the invention provides methods for treating mammalian tumors which comprise administering to a mammal having a tumor a protein kinase C inhibitory concentration of a substituted anthraquinone compound of the invention, or administering to the mammal having a tumor an amount of a compound of the invention effective to inhibit growth of the tumor.

Another embodiment of the invention provides methods of inhibiting mammalian keratinocyte proliferation which comprises administering to a mammalian keratinocyte a protein kinase C inhibitory amount of a compound of the invention, or administering to the keratinocyte an amount of a compound of the invention effective to inhibit proliferation of the keratinocyte.

Surprisingly, the compounds of the invention are not cross-resistant to adriamycin (Doxorubicin HCl, Adria Laboratories, Dublin, Ohio, an antibiotic-derived chemotherapy agent) or Mitoxantrone (Novantrone, Lederle Laboratories, Pearl River, N.Y., a synthetic anthracene dione chemotherapy agent) and remain effective in reducing growth of tumor cells resistant to these well-known chemotherapy agents. The lack of cross-resistance with adriamycin or Mitoxantrone indicates that the compounds of the invention will be particularly useful for treatment of adriamycin or Mitoxantrone resistant tumors.

Cancer is a disease characterized in part by uncontrolled cell growth. Protein kinase C is directly involved in cellular growth control and is believed to be involved in tumor formation. Protein kinase C is the major, if not exclusive, intracellular receptor of phorbol esters which are very potent tumor promoters. Phorbol esters and other tumor promoters bind to and activate protein kinase C. Since diacylglycerol (DAG) and phorbol esters interact at the sane site, DAG's have been suggested to be the "endogenous phorbol esters" by analogy with the opiate receptor where the conservation of a high affinity receptor implied the existence of an endogenous analogue. DAG has been shown to increase the affinity of protein kinase C for $Ca^{+2}$ and phospholipid and thus activates protein kinase C at cellular levels of these essential cofactors. Extracellular signals including hormones, growth factors, and neurotransmitters are known to stimulate phosphatidylinositol turnover resulting in the generation of $IP_3$ and DAG. Structures of 40 distinct oncogenes of viral and cellular origin have revealed that oncogenes encode altered forms of normal cellular proteins. Several of the gene products appear related to growth factors or other elements involved in transmembrane signalling. These oncogene products appear to function by altering the level of critical second messengers. Cells transformed with the oncogenes ras, sis, erbB, abl, and src have been shown to contain elevated levels of DAG which is then believed to activate protein kinase C. Indeed studies on ras transformed cells have shown protein kinase C activation to concomitant with elevation of DAG.

Phorbol esters, such as phorbol myristate acetate (PMA), have complex effects on cells including effects on membrane function, mitogenesis, differentiation, and gene expression. Synthetic diacylglycerols mimic many of the effects of PMA in vitro and inhibitors of protein kinase C have been shown to block PMA-induced effects on cells. Thus, protein kinase C may mediate the actions of certain oncogenes, such as ras, which cause intracellular increases in DAG and concomitant increases in protein kinase C. In addition, activation of protein kinase C leads to the expression of c-mvc, c-fos, c-cis, c-fms, nuclear protooncogenes important in cell transformation.

Overexpression of protein kinase C in NIH 3T3 cells causes altered growth regulation and enhanced tumorigenicity and in rat fibroblasts leads to anchorage-independent growth in soft agar. In these experiments, overexpression of protein kinase C in these cells resulted in tumor formation in animals receiving transplanted cells.

Several studies have shown increased expression of protein kinase C in certain tumor types such as breast and lung carcinomas. Activated protein kinase C has also been detected in human colon carcinomas although increased expression on the gene level was not seen. Topoisomerases are directly modulated by protein kinase C as substrates for the enzyme and protein kinase C inhibitors have been shown to potentiate the action of chemotherapy drugs such as cis-platinum.

New and more potent compounds which have been identified specifically as inhibitors of protein kinase C are showing early promise as therapeutic agents in inhibiting tumor growth in animal models.

Animal studies have shown that perhaps 50% or more of ischemic-related myocardial damages can be attributed to polymorphonuclear leukocytes (neutrophils) which accumulate at the site of occlusion. Damage from the accumulated neutrophils may be due to the release of proteolytic enzymes from the activated neutrophils or the release of reactive oxygen intermediates (ROI). Much of the "no reflow" phenomenon associated with myocardial ischemia is attributed to myocardial capillary plugging. The plugging of capillaries has been attributed to both aggregated platelets and aggregated neutrophils. Although both cell types are aggregated during the ischemic event, the relative contribution of each to capillary plugging has not yet been established. It is well accepted that the damage by neutrophils to myocardial tissue proceeds through a cascade of events, one of the earliest being the bonding of activated neutrophils to damaged vascular endothelium. However, the binding of the neutrophils is significantly enhanced by their activation and this an even earlier event is the generation of molecules (such as cytokines, and chemotactic factors) which can function as activation stimuli. These molecules probably originate from damaged and aggregated platelets, from damaged vascular endothelium, or from the oxidation of plasma proteins or lipids by endothelial-derived oxidants.

Strategies for overcoming the deleterious effects of reactive oxygen intermediates have centered in the development of scavengers for the molecules. Superoxide dismutase (SOD) has been shown to be a particularly effective scavenger of superoxide, but suffers from a very short half-life in the blood. Several companies have tackled this problem by creating versions of this enzyme with increased half-lives by techniques such as liposome encapsulation or polyethylene glycol conjugation. Reports on the effectiveness of these new version are mixed. Catalase, a scavenger of hydrogen peroxide, and hydroxyl radical scavengers have also been tested and found to be effective to varying degrees. However, none of the strategies designed to scavenge reactive oxygen intermediates will prevent the aggregation of platelets, the release of chemotactic molecules, the activation and adherence of neutrophils to vascular endothelium, or the release of proteolytic enzymes from activated neutrophils.

The advantage of protein kinase C inhibitors as therapeutics for reperfusion injury is that they have been demonstrated to 1) block platelet aggregation and release of neutrophil activating agents such as PAF, 2) clock neutrophil activation, chemotactic migration, and adherence to activated or damaged endothelium, and 3) block neutrophil release of proteolytic enzymes and reactive oxygen intermediates. Thus these agents have the capability of blocking all three of the most significant mechanisms of pathogenesis associated with reperfusion injury and should thus have a decided therapeutic advantage.

Figure 2:
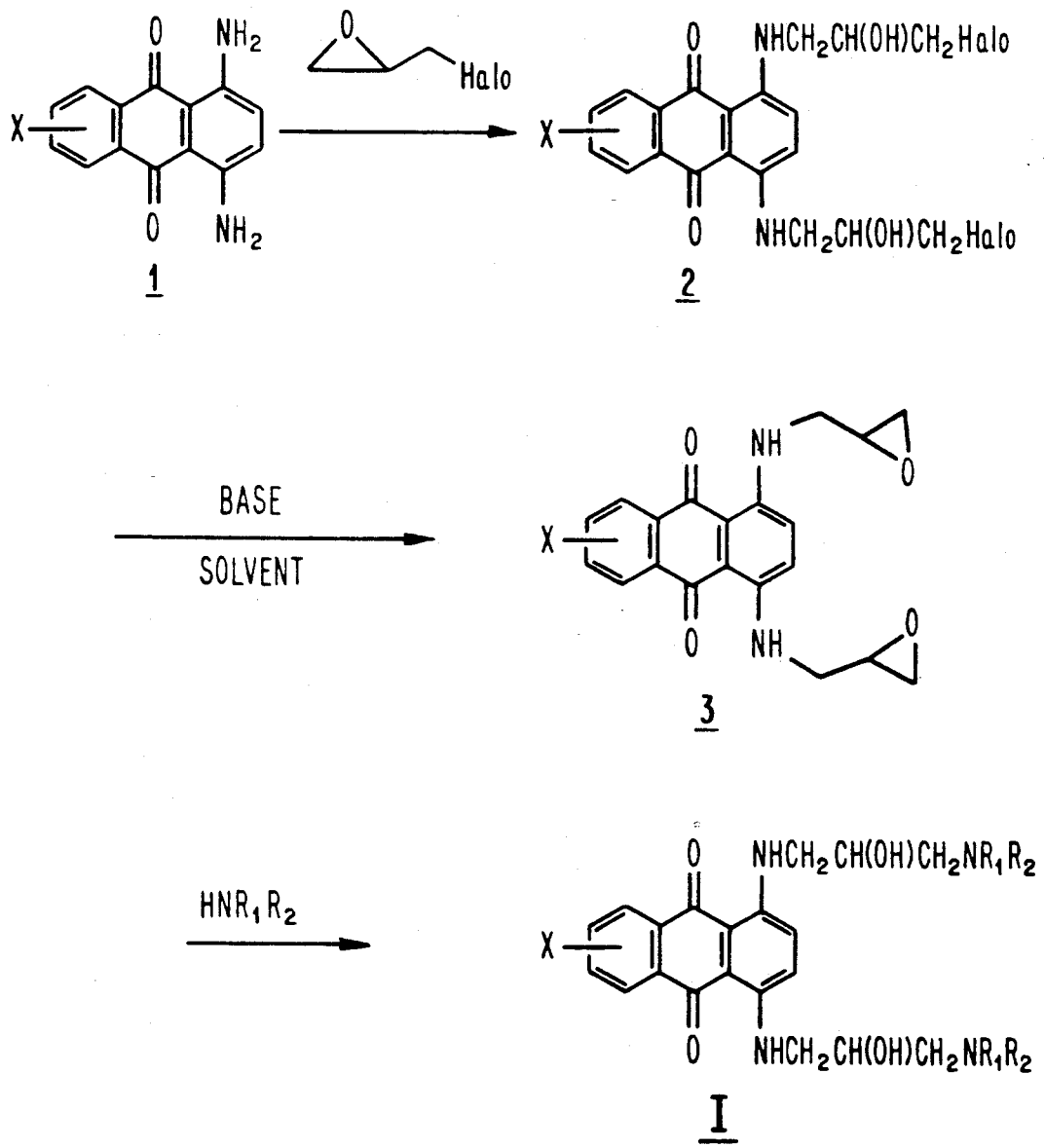
FIG. 2 shows the synthetic route of Scheme II which is used for synthesis of compounds of the invention.

The novel bis-aminoanthraquinones of the invention may be prepared according to Scheme I shown in FIG. 1, or scheme II shown in FIG. 2. The compounds of the invention may also be prepared by other methods known in the art. As used herein, the anthraquinone ring structure has the conventional ring numbering as illustrated in the *Merck Index, Tenth Edition*, Merck & Co., Inc. Rahway, N.J., 1983, pp.100–101.

In Scheme I, reaction of diaminoanthraquinone 1 with epihalohydrin provides bis-(3-halo-2-hydroxypropylamino)-anthraquinone 2 which upon treatment with amine, such as diethylamine, at temperatures ranging from room temperature to the boiling temperature of the solvent of choice, yields the product I. Scheme II is an alternative procedure which starts with the same starting material as in Scheme I, but the intermediate 2 is converted to the bis-epoxy compound 3 with a base such as sodium hydroxide; and the bis-epoxy compound reacted with amine to provide the compound of the invention, I. Examples of compounds of the invention that may be prepared according to Schemes I and II are listed in Table 1.

The optically active enantiomers of the compounds of the invention may be prepared according to Schemes I and II using optically active starting materials such as the commercially available optically active glycidol or epichlorohydrin.

Pharmaceutically acceptable salts of the compounds of the invention are also useful in the methods of the invention. Pharmaceutically acceptable salts useful in the invention include salts of hydrochloric acid, hydrobromic acid, fumaric acid, oxalic acid, maleic acid, succinic acid, pamoic acid, sulfuric acid and phosphoric acid.

TABLE 1

| Exp | $R^1$ | $R^2$ | X | m | n | MP (°C.) |
|---|---|---|---|---|---|---|
| 1a | H | Pr | H | 1 | 1 | Hygroscopic |
| 1b | H | PhCH$_2$ | H | 1 | 1 | 86–89 |
| 1c | H | PhCH$_2$ | 7-Cl | 1 | 2 | |
| 1d | Et | Et | 5-HO | 2 | 2 | |
| 1e | PhCH$_2$ | PhCH$_2$ | NMe$_2$ | 3 | 3 | |
| 1f | Ph(CH$_2$)$_3$ | H | MeO | 1 | 3 | |
| 1g | PhCH$_2$ | PhCH$_2$ | 6,7-di-HO | 1 | 1 | |
| 1h | PhCH$_2$ | H | 5,8-di-HO | 1 | 1 | |
| 1i | 2-PyrCH$_2$ | H | 5-COOH | 2 | 2 | |

(Abbreviations used in Table 1. Pr-propyl; Ph-phenyl; Et-ethyl, Pyr-pyridinyl)

The compounds of the invention may be administered by any method that produces contact of the active ingredient with the agent's site of action in the body of a mammal including but not limited to oral, intravenous, and intraparenteral. The compounds may be administered singly, or in combination with other compounds of the invention, other pharmaceutical compounds, such as chemotherapy compounds, or therapies, such as radiation treatment. The compounds are preferably administered with a pharmaceutically acceptable carrier selected on the basis of the selected route of administration and standard pharmaceutical practice.

The compounds of the invention are administered to mammals, preferably humans, in therapeutically effective amounts or concentrations which are effective to inhibit protein kinase C, or to inhibit tumor cell growth, inhibit inflammation of tissue, inhibit keratinocyte proliferation, inhibit oxidative burst from neutrophils or inhibit platelet aggregation. The dosage administered in any particular instance will depend upon factors such as the pharmacodynamic characteristics of the particular compound of the invention, and its mode and route of administration; age, health, and weight of the recipient; nature and extent of symptoms; kind of concurrent treatment, frequency of treatment, and the effect desired. It is contemplated that the daily dosage of the compounds will be in the range of from about 5 to about 400 mg per kg of body weight, preferably from about 10 to about 200 mg per kg body weight, and more preferably from about 10 to about 50 mg per kg per day, and preferably administered in divided doses 2 to 4 times a day or in sustained release form. The compounds of the invention may be administered orally in solid dosage forms, such as capsules, tablets, and powders, or in liquid dosage forms, such as elixirs, syrups, and suspensions. They may also be administered parenterally in sterile liquid dosage forms.

The compounds of the invention may be formulated into dosage forms according to standard practices in the field of pharmaceutical preparations. See Remington's Pharmaceutical Sciences, A. Osol, Mack Publishing Company, Easton, Pa., a standard reference text in this field.

For example, the compounds of the invention may be mixed with powdered carriers, such as lactose, sucrose, mannitol, starch, cellulose derivatives, magnesium stearate, and stearic acid for insertion into gelatin capsules, or for forming into tablets. Both tablets and capsules may be manufactured as sustained release products for continuous release of medication over a period of hours. Compressed tablets can be sugar coated or film coated to mask any unpleasant taste and protect the tablet from the atmosphere or enteric coated for selective disintegration in the gastrointestinal tract.

Liquid dosage forms for oral administration may contain coloring and flavoring to increase patient acceptance, in addition to a pharmaceutically acceptable diluent such as water, buffer or saline solution.

For parenteral administration, the compounds of the invention may be mixed with a suitable carrier or diluent such as water, a oil, saline solution, aqueous dextrose (glucose), and related sugar solutions, and glycols such as propylene glycol or polyethylene glycols. Solutions for parenteral administration contain preferably a water soluble salt of the compound of the invention. Stabilizing agents, antioxidizing agents and preservatives may also be added. Suitable antioxidizing agents include sodium bisulfite, sodium sulfite, and ascorbic acid, citric acid and its salts, and sodium EDTA. Suitable preservatives include benzalkonium chloride, methyl- or propyl-paraben, and chlorbutanol.

EXAMPLES

The following are specific examples which are illustrative of the present invention and are not intended to limit the scope of the invention.

EXAMPLE 1 SYNTHESIS OF 1,4-BIS-(3-CHLORO-2-HYDROXYLAMINO-PROPYLAMINO-9, 10-ANTRACENEDIONE (COMPOUND 2 IN SYNTHETIC SCHEMES I AND II)

Ephichlorohydrin (84.5 mL, 1.08 mol) was added at room temperature to a solution of 1,4 diaminoanthraquinone (10g, 42 mmol) (Aldrich Chemical Company, Milwaukee, Wis.) in glacial acetic acid (200 mL). The solution was stirred for 30 minutes at 90° C. and the solvent was removed under reduced pressure. The product was purified by flash chromatography (silica gel, $CH_2Cl_2$:MeOH/25:1) and recrystallized from $CH_2Cl_2$-Ether-Hexanes to give a pure blue solid of the title compound, 1,4-Bis-(3-Chloro-2-Hydroxy-propylamino)-9, 10-anthracenedione, (12.46 g, 70%), mp 167°–169° C.: $^1$H NMR($CDCl_3$) δ 3.21 (broad, 2H, OH), 3.5–3.6 (m, 6H, CHCH$_2$) 3.75 (d, J=3Hz, 4H, CH$_2$), 4.19 (broad, 2H, NH), 7.03 (d, J=3.2Hz, 2H, ArH (2,3)), 7.69 (m, 2H ArH, (6,7)), 8.27 (m, 2H, ArH (5,8)). Anal. Calcd for $C_{20}H_{20}O_4N_{20}Cl_2 \times 0.25\ H_2O$: C, 56 15; H, 4.83; N, 6.55. Found: C, 56.18; H, 4.76;; N, 6.29.

EXAMPLE 2 SYNTHESIS OF 1,4 BIS-(2,3-EPOXYPROPYLAMINO)-9,10-ANTHRACENEDIONE (COMPOUND 3 IN SYNTHETIC SCHEME II)

To a solution of 1,4-Bis-(3-chloro-2-hydroxyl-propylamino)-9, 10-anthracenedione (8.3 g, 19.8 mmoles) in MeOH (500 mL) at 60° C. was added NaOH (3.5 g). The resulting blue solution was stirred at room temperature for 4 hours, and the solvent was removed under reduced pressure. The residual solid was then purified by flash column chromatography (silica gel, $CH_2Cl_2$: MeOH/25:1). Recrystalization from $CH_2Cl_2$:hexanes yielded the title compound 1,4-Bis-(2,3-epoxypropylamino)-9, 10-anthracenedione, (6.2 g, 89.37%), mp 189°–190° C.: $^1$H NMR ($CDCl_3$) δ 2.74 (m, 1H, CH$_2$), 2.87 (m, 1H, CH$_2$), 3.26 (m, 1H, CH) 3.57 (m, 1H, CH$_2$), 3.78 (m, 1H, CH$_2$), 7.32 (s, 2H, Ar 2, 3)), 7.71 (dd, J=3.2 Hz, 5.5 Hz, 2H, Ar 6, 7)), 8.34 (dd, J=3.2 Hz, 5.5 Hz, 2H, Ar (5,8)), 10.76 (s, 2H, NH). Anal. Calcd for $C_{20}H_{18}O_4N_2 \times 0.25\ H_2O$: C, 67.66: H, 5.25; N, 7.93. Found: C, 67.72; H, 5.55; N, 7.54. IR: 3400, 3070, 2910, 1640, 1220, 900.

EXAMPLE 3 SYNTHESIS OF 1,4-BIS-(3-PROPYLAMINO-2-HYDROXY-PROPYLAMINO)-9, 10 ANTHRACENEDIONE HYDROCHLORIDE SALT (COMPOUND 1a IN TABLE 1)

To a solution of 1,4-bis-(3-chloro-2-hydroxyl-propylamino)-9, 10-anthracenedione (1 g, 2.36 mmole), propylamine (1.39 g, 23.6 mmole), and potassium iodide (0.26 g, 160 mmole) in methanol (20 mL), which had been stirred for 4 hours at room temperature, was added potassium carbonate (0.5 g, 3.62 mmole), and the reaction was stirred at room temperature for an additional 16 hours. Solvent was removed and the blue product was dissolved in dichloromethane, and was washed three times with water. The organic layer was dried over magnesium sulfate and the solvent was removed under reduced pressure. The blue product was purified by column chromatography (silica gel, dichloromethane with an increasing methanol gradient) to yield the free base of the title compound, which was then treated with hydrochloride gas through a stirring solution in acetone until a color change was noted to yield the title compound 1,4-Bis-(3-Propylamino-2-Hydroxy-propylamino)-9, 10 anthracenedione hydrochloride (580 mg, 48%); NMR ($CDCl_3$) δ 0.94 (t, J=7.3 Hz, 6H, CH$_3$), 1.57 (m, 4H, CH$_2$), 2.64 (m, 4H, CH$_2$), 2.75 (m, 4H, CH$_2$), 3.33 (m, 6H, CH and CH$_2$), 4.05 b, 2H, OH), 6.80 (s, 2H, Ar (2, 3)), 7.52 (m, 2H, Ar (6, 7)), 7.94 (m, 2H, Ar (5, 8)), 10.63 (b, 2H, NH);

EXAMPLE 4 1,4-BIS-(3-BENZYLAMINO-2-HYDROXY-PROPYLAMINO)-9, 10 ANTRACENEDIONE HYDROCHLORIDE SALT (COMPOUND 1b IN TABLE 1)

To a solution of 1,4-bis-(3-chloro-2-hydroxypropylamino)-9, 10-anthracenedione (1 g, 2.36 mmole), benzylamine (2.02 g, 18.88 mmole), and potassium iodide (0.25 g, 153 mmole) in a solution of methanol (40 mL) and dichloromethane (5 mL), which had been heated at reflux for 5 hours, was added potassium carbonate (0.7 g, 5.06 mmole). The reaction was heated at reflux for an additional 16 hours. Solvent was removed and the blue product was dissolved in dichloromethane and washed three times with water. The organic layer was dried over magnesium sulfate and the solvent was removed under reduced pressure. The blue free base product was purified by column chromatography (silica gel, dichloromethane with an increasing methanol gradient). The title product 1,4-Bis-(3-Benzylamino-2-Hydroxypropylamino)-9, 10 anthracenedione. Hydrochloride salt (610 mg, 42% yield) was formed by bubbling hydrochloride gas through a stirring solution of the free base in acetone until a color change was noted, mp 86°–89° C.; NMR ($CDCl_3$) δ 2.76 (m, 2H, CH$_2$) 2.90 (m, 2H CH$_2$), 3.43 (m, 6H, CH$_2$and OH), 3.85 (d, J=4.3 Hz, 4H, CH$_2$), 4.04 (m, 2H, CH), 7.15 (s, 2H, Ar (2, 3)), 7.31 (m, 10H, Ar (Benzyl)), 7.64 (m, 2H, Ar (6 ,7)), 8.22 (m, 2H, Ar (5, 8)), 10.82 (b, 2H, NH); Anal. Calcd for $C_{34}H_{37}N_4O_4 \times HCl$: C, 67.93; H, 6.20; N, 9.32. Found: C, 68.21; H, 6.14; N, 9.02.

EXAMPLE 5 PROTEIN KINASE C INHIBITION

The protein kinase C (PKC) assay is designed to duplicated the in vivo conditions required for protein kinase C function. Therefore, pH, salt and cofactor concentrations are similar to physiologic levels. Histone H1 (lysine rich) is used in the assay as the phosphorylation acceptor protein because it is readily available and serves as a good substrate for protein kinase C. The enzyme is prepared from rat brain and is purified to apparent homogeneity as determined by a single band on silver stained SDS-polyacrylamide. Studies on the mechanism of regulation of protein kinase C by phospholipids, DAG and $Ca^{+2}$ have been hampered by the physical properties of the lipid cofactors. In the screening assay, phosphatidylserine (PS) and DAG are cosonicated to form unilamellar and multilamellar vesicles. The concentration of lipids in the assay are suboptimal to maximize the detection potential of the assay for inhibitors. Potential inhibitor compounds are added to the assay in dimethylsulfoxide at three concentrations to give final inhibitor concentrations of 4.3, 43 and 218

μM. respectively. The assay is started with the addition of enzyme and stopped after 10 min by the addition of 25% trichloroacetic acid (TCA) and 1.0 mg/ml bovine serum albumin (BSA). The radioactive histone product is retained and washed on glass fiber filters that allow the unreacted $^{32}$P-ATP to pass through. The amount of phosphorylation is determined by the radioactivity measured in a scintillation counter. Controls are included in every assay to measure background activity in the absence of enzyme, activity in the absence of lipids and the maximum enzyme activity with saturating levels of the activator lipids. Assay components and concentrations are given in Table 3.

TABLE 3

| Assay Component | Concentration |
| --- | --- |
| Hepes pH 7.5 | 20 mM |
| MgCl$_2$ | 20 mM |
| CaCl$_2$ | 100 μM |
| EGTA | 95 μM |
| Histone H1 | 200 μg/ml |
| Phosphatidylserine | 40 μg/ml |
| Diacylglycerol | 1.8 μg/ml |
| Protein Kinase C | 0.6 μg/ml |
| γ-$^{32}$P-ATP | 20 μM |

Results of the protein kinase c assay are shown in Table 5 in the column labeled PKC. Results are shown as IC$_{50}$, which is the concentration of test compound needed to inhibit 50% of the protein kinase C activity as compared with levels of protein kinase C activity in controls. Compounds of the invention were able to effectively inhibit protein kinase activity. As shown in Table 5, compound 1a had an IC$_{50}$ of 199 μM, and compound 1b had an IC$_{50}$ of 43 μM.

TABLE 5

| | IC$_{50}$ (μM) | |
| --- | --- | --- |
| Exp. | PKC | PKA |
| 1a | 199 | n.e. |
| 1b | 43 | n.e. |

EXAMPLE 6 cAMP (DEPENDENT PROTEIN KINASE (PKA) ASSAY

Compounds found to be inhibitors of protein kinase C are tested for inhibitory activity against protein kinase (PKA). This enzyme, like protein kinase C, plays an important role in cell-cell communication and is activated by a second messenger, cAMP. Secondary screening against PKA is useful for ascertaining the selectivity of the compounds of the invention. The standard assay conditions are given in Table 6. The catalytic subunit of PKA (Sigma Chemical Company, St. Louis, Mo.) is mixed with buffer before addition of the inhibitor in dimethylsulfoxide (DMSO). The assay is started by the addition of 32P-ATP and the reaction is allowed to proceed for 10 min before stopping with 25% trichloroacetic acid (TCA) and 1.0 mg/ml bovine serum albumin (BSA). The phosphorylated protein is isolated by filtration and the radioactivity is counted in a beta scintillation counter.

TABLE 6

| Assay Components | Concentration |
| --- | --- |
| Hepes pH 7.5 | 20 mM |
| Histone H1 | 200 μg/ml |
| Dithiothreitol | 32 μg/ml |
| Protein Kinase A | 2.6 μg/ml |

TABLE 6-continued

| Assay Components | Concentration |
| --- | --- |
| γ-$^{32}$-ATP | 20 μM |

Results of the PKA assay are shown in Table 5 (in Example 5) in the column labeled PKA. As shown in Table 5, the compounds of the invention that were tested had no effect on PKA. The tested compounds of the invention are selective for protein kinase c, and have no effect on cAMP dependent protein kinase. The compounds of the invention should thus have no effect on the metabolic pathways associated with stimulation of protein kinase by cAMP.

EXAMPLE 7 HUMAN TUMOR CELL GROWTH INHIBITION

MCF-7 a human breast tumor cell line and MCF-7/ADR an adriamycin resistant line of MCF-7 cells were obtained from the National Cancer Institute, Frederick, Md. CEM cells (ATCC accession number CCL 119) were obtained from the American Type Culture Collection, Rockville, Md.

Human tumor cells are trypsinized (0.05% trypsin, GIBCO), counted with a hemacytometer and seeded at a concentration of 10,000 cells/well in a 96 well microtiter plate. After allowing cells to attach to the surface overnight, the culture medium is aspirated and replaced with 100 μl of fresh medium. Test agents are diluted to determine dose response at 2× final concentration and added in quadruplicate at 100 μl/well to bring the total volume of each well to 200 μl. The microtiter plate is then incubated at 37° C. 5% CO$_2$ overnight (18-24 hrs) before $^3$H-thymidine is added at a concentration of 0.5 μCi/well in 50 μl culture medium. The plate is incubated again for 4 hrs under the same conditions as above. Supernatant is then aspirated and 50μl trypsin (0.05%, GIBCO) is added to each well. Cells are checked microscopically to determine detachment from surfaces, and plates are then harvested with a cell harvester (PHD, Cambridge Technology, Inc.) Filter papers corresponding to wells are placed in scintillation vials and counted to determine the amount of $^3$H-thymidine incorporated by the cells. Test agent response is compared to a positive control of cell wells with culture media only to determine the IC$_{50}$. IC$_{50}$ is the concentration of test compound required to inhibit fifty per cent of the incorporation of $^3$H-thymidine into proliferating cells not exposed to test agent. Uptake of $^3$H-thymidine is a standard test for measuring the metabolism of cells. Cells which are actively proliferating take up $^3$H-thymidine, whereas cells that are not proliferating take up $^3$H-thymidine at much slower rates or not at all. Test agents that inhibit the uptake of $^3$H-thymidine thus slow the growth of cells.

As shown in Table 7, compounds of the invention were able to inhibit $^3$H-thymidine uptake and thus inhibit the proliferation of the tested cell lines. When tested with cell lines CEM and MCF-7, compound 1a had an IC$_{50}$ of 5.6 μM and 2.4 μM, respectively. However, when tested with MCF-7/ADR, the IC$_{50}$ was greater than 25 μM. The results with compound 1b were similar. When tested with CEM and MCF-7 cells, the IC$_{50}$ was 2.7 μM in both instances, however the IC$_{50}$ was 17.0 μM when compound 1b was tested with cell line MCF-7/ADR.

TABLE 7

| Compound | IC$_{50}$ ($\mu$M) | | |
|---|---|---|---|
| | CEM | MCF-7 | MCF-7/ADR |
| 1a | 5.6 | 2.4 | >25 |
| 1b | 2.7 | 2.7 | 17.0 |

EXAMPLE 8 HUMAN KERATINOCYTE INHIBITION

Proliferating keratinocytes (NHEK cells purchased from Clonetics, Inc., San Diego, Calif.) in second passage were grown in Keratinocyte Growth Medium (KGM) (Clonetics, Inc.) Cells are trypsinized (0.025% trypsin, Clonetics), counted with a hemacytometer (Scientific Products), and seeded at a concentration of 2,500 cells/well in a 96 well microtiter plate. After allowing cells to attach to the surface overnight, the culture medium is aspirated and replaced with 100 $\mu$l of fresh KGM. Test agents are evaluated and IC$_{50}$'s are determined according to the $^3$H-thymidine incorporation procedures described as in Example 7. IC$_{50}$ is the concentration of test compound required to inhibit fifty per cent of the incorporation of $^3$H-thymidine into proliferating cells not exposed to test agent.

Compound 1b had an IC$_{50}$ of 4.0 $\mu$M and thus was effective in slowing the proliferation of the cells. These results indicate that compounds of the invention are active against human keratinocytes, and will be useful in treating topical inflammatory conditions such as psoriasis and other conditions where hyperproliferation of keratinocytes is a symptom.

EXAMPLE 9 NEUTROPHIL SUPEROXIDE ANION (O$_2$—) RELEASE ASSAY

Neutrophils are isolated form whole blood collected from human volunteers. All reagent materials are obtained from Sigma Chemical Company with the exception of isotonic saline (Travenol Laboratories, Inc., Deerfield, Ill.) and lymphocyte separation medium (Organon Teknika, Durham, N.C.).

NEUTROPHIL ISOLATION

Whole blood is drawn and mixed with sodium heparin (final conc. 10 units/ml) to prevent clotting. An equal volume of dextran (3.0%) in isotonic saline is added, mixed, and allowed to settle for 30 min to bind red blood cells (RBC). Supernatant is removed, underlayered with lymphocyte separation medium and centrifuged for 40 min at 400 $\times$g in a centrifuge (Beckman GPR, Norcross, Ga.). The pellet is alternately resuspended in 0.2% and 1.6% NaCl to lyse RBCs before washing with Hank's Balanced Salt Solution (HBSS). The washed pellet is resuspended in 10 ml HBSS and placed on ice before counting on a hemacytometer.

ASSAY PROCEDURE

The neutrophil cell concentration is adjusted to 2$\times$10$^6$ cells/ml with HBSS before adding 0.8 ml cells to 12$\times$75 mm polypropylene test tubes (Fisher Scientific). Test agents are diluted to determine dose response and added at 10$\times$ final concentration at a volume of 0.1 ml/tube in duplicate. Then 10$\times$ concentrations of cytochrome C (15 mg/ml) with catalase (3000 units/ml) either alone or containing 25 ng/ml phorbol 12-myristate 13-acetate (PMA) are added at a volume of 0.1 ml/tube and incubated at 37° C. for 30 min before stopping the reaction by placing tubes on ice. Tubes are then centrifuged at 900 $\times$g for 10 min, 0.5 ml supernatant is removed and added to 0.5 ml H$_2$O in a microcuvette. Optical density (OD) of cytochrome c is read in a spectrophotometer (Shimadzu) at 550 nm. The $\Delta$OD of cytochrome c is obtained between PMA-stimulated and non-stimulated tubes, and the dose responses of the test agents are compared to the positive controls (which contain HBSS in place of test agents). PMA stimulates O$_2$$^-$ production which reduces cytochrome c. Reducing cytochrome c increases its absorbance, and the change in OD of cytochrome c is proportional to the amount of O$_2$$^-$ produced by PMA stimulation. Inhibition of the O$_2$$^-$ burst by test compounds of the invention is seen as a reduction in the change in optical density. Inhibition is expressed as IC$_{50}$ $\mu$M and is the amount of test compound that will inhibit fifty per cent of the PMA-stimulated respiratory outburst, i.e. O$_2$$^-$ production.

The tested compound was able to inhibit O$_2$$^-$ production by PMA-stimulated neutrophils. Compound 1b had an IC$_{50}$ of 3.9 $\mu$M.

We claim:

1. A substituted anthraquinone having the formula wherein
R$_1$ and R$_2$ are independently H, alkyl, aryl, or arylalkyl;
m and n are independently 1, 2, or 3;
X is H, OH, NR$_3$R$_4$, Cl, Br, I, F, alkyl, aryl alkoxy, aroxy, COOR$_5$, or CONR$_6$R$_7$;
R$_3$, R$_4$, R$_5$, R$_6$, and R$_7$ are independently H, lower alkyl or aryl.

2. The substituted anthraquinone of claim 1 wherein R$_1$ and R$_2$ independently are H, lower alkyl, or arylalkyl;
m and n are independently 1 or 2; and
X is H, OH, Cl, Br, I, F, or alkoxy.

3. The substituted anthraquinone of claim 2 wherein R$_1$ and R$_2$ independently are H or arylalkyl;
m and n are 1; and
X is H or OH.

4. A pharmaceutical composition for inhibiting protein kinase C comprising a substituted anthraquinone of claim 1 and a pharmaceutically acceptable carrier or diluent.

5. A pharmaceutical composition for inhibiting protein kinase C comprising a substituted anthraquinone of claim 2 and a pharmaceutically acceptable carrier or diluent.

6. A pharmaceutical composition for inhibiting protein kinase C comprising a substituted anthraquinone of claim 3 and a pharmaceutically acceptable carrier or diluent.

7. A method of inhibiting protein kinase C which comprises contacting protein kinase C with an inhibitory amount of a substituted anthraquinone having the formula

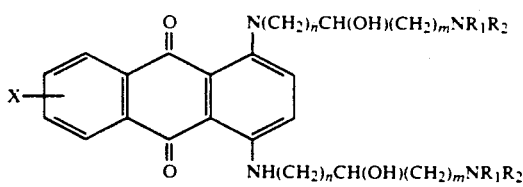

wherein

R₁ and R₂ are independently H, alkyl, aryl, or arylalkyl;

m and n are independently 1, 2, or 3;

X is H, OH, NR₃R₄, Cl, Br, I, F, alkyl, aryl alkoxy, aroxy, COOR₅, or CONR₆R₇;

R₃, R₄, R₅, R₆, and R₇ are independently H, lower alkyl or aryl.

8. The method of claim 7 wherein

R₁ and R₂ independently are H, lower alkyl, or arylalkyl;

m and n are independently 1 or 2; and

X is H, OH, Cl, Br, I, F, or alkoxy.

9. The method of claim 8 wherein

R₁ and R₂ independently are H or arylalkyl;

m and n are 1; and

X is H or OH.

10. A method of inhibiting an oxidative burst in neutrophils which comprises contacting a neutrophil with a protein kinase C inhibitory concentration of a substituted anthraquinone having the formula

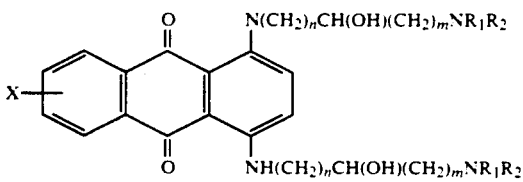

wherein

R₁ and R₂ are independently H, alkyl, aryl, or arylalkyl;

m and n are independently 1, 2, or 3;

X is H, OH, NR₃R₄, Cl, Br, I, F, alkyl, aryl alkoxy, aroxy, COOR₅, or CONR₆R₇;

R₃, R₄, R₅, R₆, and R₇ are independently H, lower alkyl or aryl.

11. The method of claim 10 wherein

R₁ and R₂ independently are H, lower alkyl, or arylalkyl;

m and n are independently 1 or 2; and

X is H, OH, Cl, Br, I, F, or alkoxy.

12. The method of claim 11 wherein

R₁ and R₂ independently are H or arylalkyl;

m and n are 1; and

X is H or OH.

13. A method of inhibiting an oxidative burst in neutrophils which comprises contacting a neutrophil with an amount of a compound of claim 1 effective to inhibit said oxidative burst.

14. A method of inhibiting an oxidative burst in neutrophils which comprises contacting a neutrophil with an amount of a compound of claim 2 effective to inhibit said oxidative burst.

15. A method of inhibiting an oxidative burst in neutrophils which comprises contacting a neutrophil with an amount of a compound of claim 3 effective to inhibit said oxidative burst.

16. A method for treating inflammation which comprises administering to a mammal suffering from inflammation a protein kinase C inhibitory concentration of a substituted anthraquinone having the formula

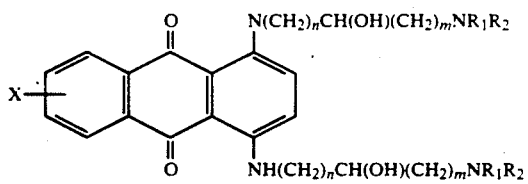

wherein

R₁ and R₂ are independently H, alkyl, aryl, or arylalkyl;

m and n are independently 1, 2, or 3;

X is H, OH, NR₃R₄Cl, Br, I, F, alkyl, aryl alkoxy, aroxy, COOR₅, or CONR₆R₇;

R₃, R₄, R₅, R₆, and R₇ are independently H, lower alkyl or aryl.

17. The method of claim 16 wherein

R₁ and R₂ independently are H, lower alkyl, or arylalkyl;

m and n are independently 1 or 2; and

X is H, OH, Cl, Br, I, F, or alkoxy.

18. The method of claim 17 wherein

R₁ and R₂ independently are H or arylalkyl;

m and n are 1; and

X is H or OH.

19. A method for treating inflammation which comprises administering to a mammal suffering from inflammation an amount of a compound of claim 1 effective to inhibit inflammation.

20. A method for treating inflammation which comprises administering to a mammal suffering from inflammation an amount of a compound of claim 2 effective to inhibit inflammation.

21. A method for treating inflammation which comprises administering to a mammal suffering from inflammation an amount of a compound of claim 3 effective to inhibit inflammation.

22. A method for inhibiting growth of mammalian tumor cells which comprises contacting a mammalian tumor cell with a protein kinase C inhibitory concentration of a substituted anthraquinone having the formula

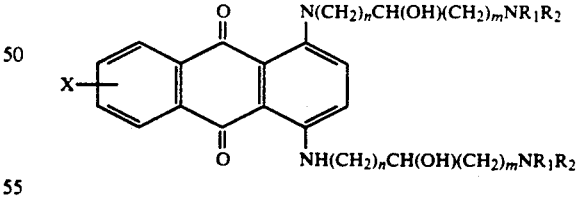

wherein

R₁ and R₂ are independently H, alkyl, aryl, or arylalkyl;

m and n are independently 1, 2, or 3;

X is H, OH, NR₃R₄, Cl, Br, I, F, alkyl, aryl alkoxy, aroxy, COOR₅, or CONR₆R₇;

R₃, R₄, R₅, R₆, and R₇ are independently H, lower alkyl or aryl.

23. The method of claim 22 wherein

R₁ and R₂ independently are H, lower alkyl, or arylalkyl;

m and n are independently 1 or 2; and

X is H, OH, Cl, Br, I, F, or alkoxy.

24. The method of claim 23 wherein
$R_1$ and $R_2$ independently are H or arylalkyl;
m and n are 1; and
X is H or OH.

25. A method for inhibiting growth of mammalian tumor cells which comprises contacting a mammalian tumor cell with an amount of a compound of claim 1 effective to inhibit growth of said mammalian tumor cell.

26. A method for inhibiting growth of mammalian tumor cells which comprises contacting a mammalian tumor cell with an amount of a compound of claim 2 effective to inhibit growth of said mammalian tumor cell.

27. A method for inhibiting growth of mammalian tumor cells which comprises contacting a mammalian tumor cell with an amount of a compound of claim 3 effective to inhibit growth of said mammalian tumor cell.

28. A method for treating mammalian tumors which comprises administering to a mammal having a tumor a protein kinase C inhibitory concentration of a substituted anthraquinone having the formula

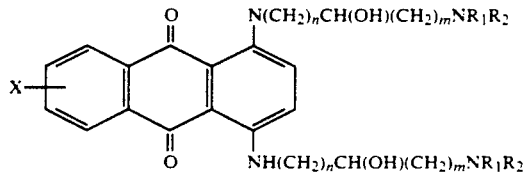

wherein
$R_1$ and $R_2$ are independently H, alkyl, aryl, or arylalkyl;
m and n are independently 1, 2, or 3;
X is H, OH, $NR_3R_4$, Cl, Br, I, F, alkyl, aryl alkoxy, aroxy, $COOR_5$, or $CONR_6R_7$;
$R_3$, $R_4$, $R_5$, $R_6$, and $R_7$ are independently H, lower alkyl or aryl.

29. The method of claim 28 wherein
$R_1$ and $R_2$ independently are H, lower alkyl, or arylalkyl;
m and n are independently 1 or 2; and
X is H, OH, Cl, Br, I, F, or alkoxy.

30. The method of claim 29 wherein
$R_1$ and $R_2$ independently are H or arylalkyl;
m and n are 1; and
X is H or OH.

31. A method for treating mammalian tumors which comprises administering to a mammal having a tumor an amount of a compound of claim 1 effective to inhibit growth of said tumor.

32. A method for treating mammalian tumors which comprises administering to a mammal having a tumor an amount of a compound of claim 2 effective to inhibit growth of said tumor.

33. A method for treating mammalian tumors which comprises administering to a mammal having a tumor an amount of a compound of claim 3 effective to inhibit growth of said tumor.

34. A method of inhibiting keratinocyte proliferation comprising administering to a keratinocyte a protein kinase C inhibitory amount of a compound having the formula

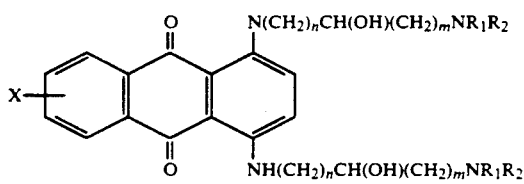

wherein
$R_1$ and $R_2$ are independently, H, alkyl, aryl, or arylalkyl;
m and n are independently 1, 2, or 3;
X is H, OH, $NR_3R_4$, Cl, Br, I, F, alkyl, aryl alkoxy, aroxy, $COOR_5$, or $CONR_6R_7$;
$R_3$, $R_4$, $R_5$, $R_6$, and $R_7$ are independently H, lower alkyl or aryl.

35. The method of claim 33 wherein
$R_1$ and $R_2$ independently are H, lower alkyl, or arylalkyl;
m and n are independently 1 or 2; and
X is H, OH, Cl, Br, I, F, or alkoxy.

36. The method of claim 35 wherein
$R_1$ and $R_2$ independently are H or arylalkyl;
m and n are 1; and
X is H or OH.

37. A method of inhibiting mammalian keratinocyte cell proliferation comprising administering to said keratinocyte an amount of a compound of claim 1 effective to inhibit proliferation of said keratinocyte.

38. A method of inhibiting mammalian keratinocyte cell proliferation comprising administering to said keratinocyte an amount of a compound of claim 2 effective to inhibit proliferation of said keratinocyte.

39. A method of inhibiting mammalian keratinocyte cell proliferation comprising administering to said keratinocyte an amount of a compound of claim 3 effective to inhibit proliferation of said keratinocyte.

* * * * *